United States Patent [19]
Romano et al.

[11] Patent Number: 6,103,683
[45] Date of Patent: *Aug. 15, 2000

[54] DISINFECTING COMPOSITIONS AND PROCESSES FOR DISINFECTING SURFACES

[75] Inventors: Nicoletta Romano; Marina Trani; Giovanni Minervini, all of Rome, Italy; Marena Dessette Brown, Fairfield, Ohio

[73] Assignee: The Procter & Gamble Co., Cincinnati, Ohio

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 09/101,559

[22] PCT Filed: Jan. 8, 1997

[86] PCT No.: PCT/US97/00214

§ 371 Date: Jul. 13, 1998

§ 102(e) Date: Jul. 13, 1998

[87] PCT Pub. No.: WO97/25404

PCT Pub. Date: Jul. 17, 1997

[30] Foreign Application Priority Data

Jan. 12, 1996 [EP] European Pat. Off. ............. 96870001
Feb. 23, 1996 [EP] European Pat. Off. ............. 96870017

[51] Int. Cl.$^7$ ............................... C11D 1/90; C11D 1/92; C11D 3/48; C11D 7/18
[52] U.S. Cl. ................... 510/383; 510/101; 510/104; 510/131; 510/159; 510/295; 510/309; 510/319; 510/490; 510/504
[58] Field of Search ................... 510/101–107, 510/131, 133, 138, 159, 161, 281, 283, 284, 295, 309, 319, 372, 373, 383, 406, 490, 503, 504

[56] References Cited

U.S. PATENT DOCUMENTS

| | | | |
|---|---|---|---|
| Re. 35,000 | 7/1995 | Aoyagi et al. | 252/99 |
| 3,912,666 | 10/1975 | Spitzer et al. | 260/2.5 E |
| 3,977,826 | 8/1976 | Iscowitz | 8/10.2 |
| 4,230,478 | 10/1980 | Zumbrunn | 71/3 |
| 4,347,149 | 8/1982 | Smith et al. | 252/102 |
| 4,430,236 | 2/1984 | Franks | 252/95 |
| 4,470,919 | 9/1984 | Goffinet et al. | 252/102 |
| 4,477,438 | 10/1984 | Wilcockson et al. | 242/130 |
| 4,537,778 | 8/1985 | Clipper et al. | 424/53 |
| 4,585,648 | 4/1986 | Maeyama et al. | 424/49 |
| 4,708,880 | 11/1987 | Hussein | 426/424 |
| 4,767,617 | 8/1988 | Shansky et al. | 424/71 |
| 4,900,721 | 2/1990 | Bansemir et al. | 514/25 |
| 4,925,655 | 5/1990 | Smigel et al. | 424/52 |
| 5,085,853 | 2/1992 | Williams et al. | 424/53 |
| 5,174,990 | 12/1992 | Douglas | 424/53 |
| 5,208,010 | 5/1993 | Thaler | 424/53 |
| 5,246,552 | 9/1993 | Kamiya et al. | 204/131 |
| 5,256,402 | 10/1993 | Prencipe et al. | 424/50 |
| 5,302,373 | 4/1994 | Giacin et al. | 424/49 |
| 5,310,546 | 5/1994 | Douglas | 424/53 |
| 5,362,495 | 11/1994 | Lesage | 424/435 |
| 5,403,587 | 4/1995 | McCue et al. | 424/195 |
| 5,543,374 | 8/1996 | Wu | 502/107 |
| 5,545,374 | 8/1996 | French et al. | 422/28 |
| 5,578,134 | 11/1996 | Lentsch et al. | 134/3 |
| 5,602,090 | 2/1997 | Melikyan et al. | 510/372 |
| 5,624,906 | 4/1997 | Vermeer | 514/23 |
| 5,688,492 | 11/1997 | Galley et al. | 424/49 |
| 5,696,171 | 12/1997 | Rupp et al. | 514/700 |
| 5,814,304 | 9/1998 | Wong et al. | 424/53 |
| 5,858,330 | 1/1999 | Boltri et al. | 424/45 |

FOREIGN PATENT DOCUMENTS

| | | | |
|---|---|---|---|
| 0 667392A2 | 8/1995 | European Pat. Off. | C11D 3/39 |
| 0 842606A1 | 5/1998 | European Pat. Off. | A01N 59/00 |
| 269373B | 1/1994 | France | C11D 1/94 |
| 60-038497 | 2/1985 | Japan | C11D 3/60 |
| 60-038498 | 2/1985 | Japan | C11D 3/60 |
| 1232-266 | 5/1986 | U.S.S.R. | A61L 9/00 |
| WO 8800-795 | 2/1988 | WIPO | A01N 65/00 |
| WO 92/18091 | 10/1992 | WIPO | A61K 7/16 |
| WO 95/34276 | 12/1995 | WIPO | A61K 7/16 |
| WO 96/16633 | 6/1996 | WIPO | A61K 7/16 |
| WO 97/25396 | 7/1997 | WIPO | C11D 1/62 |
| WO 97/26855 | 7/1997 | WIPO | A61K 7/20 |
| WO 97/42280 | 11/1997 | WIPO | C11D 1/75 |
| WO 98/02044 | 1/1998 | WIPO | A01N 65/00 |

Primary Examiner—Yogendra Gupta
Assistant Examiner—Christine Ingersoll
Attorney, Agent, or Firm—John M. Hoqwll; T. David Reed; Jacobus c. Rasser

[57] ABSTRACT

The present invention relates to the disinfection of surfaces with a disinfecting composition comprising from 0.1% to 15% by weight of the total composition of hydrogen peroxide, and an antimicrobial essential oil or mixtures thereof.

17 Claims, No Drawings

DISINFECTING COMPOSITIONS AND PROCESSES FOR DISINFECTING SURFACES

TECHNICAL FIELD

The present invention relates to antimicrobial compositions which can be used to disinfect and clean various surfaces including animate surfaces (e.g., human skin, mouth and the like) and inanimate surfaces including, but not limited to, hard surfaces like walls, tiles, table tops, glass, bathroom surfaces, kitchen surfaces, dishes as well as fabrics, clothes, carpets and the like.

BACKGROUND

Antimicrobial/antibacterial compositions include materials which have the ability to disinfect. It is generally recognised that a disinfecting material greatly reduces or even eliminates the microorganisms, e.g., bacteria, existing on a surface. For example compositions based on halogen containing compounds like hypochlorite, or on quaternary compounds, have been extensively described in the art for disinfecting purpose. Compositions comprising a peracid are also known as disinfecting compositions.

However, a drawback associated to such disinfecting compositions based on peracids is that they may damage surfaces onto which they are contacted to perform their disinfecting action. Indeed such disinfecting compositions based on peracids are perceived by the consumers as being not safe to various surfaces including hard-surfaces and fabrics, especially delicate fabrics like silk, wool and the like.

It is therefore an object of the present invention to provide disinfecting compositions that deliver improved safety to the surfaces treated therewith while not compromising on the disinfection performance delivered onto said surfaces even when used upon high diluted conditions.

It has now been found that the above object can be achieved by providing a composition comprising from 0.1% to 15% by weight of the total composition of hydrogen peroxide and an antimicrobial essential oil, or mixtures thereof. More particularly, it has been found that the compositions of the present invention comprising hydrogen peroxide and said antimicrobial essential oil, deliver improved safety to the surface treated therewith, while providing also excellent disinfection on clean surfaces, i.e. surfaces being free of any organic and/or inorganic soils, even at high dilution levels, i.e. up to dilution levels of from 1:100 (composition:water).

Accordingly, the compositions according to the present invention are suitable for disinfecting all types of surfaces including animate surfaces (e.g., human skin and/or mouth when used as an oral preparation or toothpaste) and inanimate surfaces. Indeed, this technology is particularly suitable in hard-surfaces applications as well as in laundry applications, e.g., as a laundry detergent or laundry additive in a so called "soaking mode", "through the wash mode", or even as a laundry pretreater in a "pretreatment mode". More particularly, the compositions according to the present invention are suitable to be used on delicate surfaces including those surfaces in contact with food and/or babies in a safe manner. Indeed, when using the compositions according to the present invention in diluted conditions, the amount of chemical residues left onto a surface disinfected therewith is reduced. Thus, it may be not necessary to rinse for example a hard-surface after the compositions of the present invention have been applied thereto in diluted conditions.

An advantage of the present invention is that excellent disinfection is provided on a broad range of bacterial pure strains including Gram positive and Gram negative bacterial strains and more resistant micro-organisms like fungi.

Another advantage of the compositions of the present invention is that beside the disinfection properties delivered, good cleaning is also provided, especially in the embodiment of the present invention where the compositions herein further comprise a surfactant and/or a solvent.

Yet another advantage of the compositions of the present invention is that they may be provided in different forms, e.g., in a liquid form packaged in a conventional detergent bottle, or in a sprayable or foamable form packaged in a spray/foam dispenser, or in the form of wipes incorporating such a composition, or in a non-liquid form (e.g. gel, pasty form or solid form).

Representative of the prior art is for example WO88/00795 which discloses liquid disinfecting compositions comprising a compound selected from the group of organic acids, perborates, peracids and their salts, together with a quaternary ammonium salt and an essential oil. No hydrogen peroxide is disclosed in the disinfecting compositions therein, let alone levels thereof.

EP-B-288 689 discloses a liquid for hard-surfaces comprising antimicrobial effective amounts of pine oil and at least one oil soluble organic acid. No hydrogen peroxide is disclosed.

U.S. Pat. No. 5,403,587 discloses aqueous antimicrobial compositions which can be used to sanitise, disinfect, and clean hard-surfaces. More particularly, U.S. Pat. No. 5,403,587 discloses aqueous compositions (pH 1 to 12) comprising essential oils (0.02% to 5%), which exhibit antimicrobial properties efficacy such as thyme oil, eucalyptus oil, clove oil and the like, and a solubilizing or dispersing agent sufficient to form an aqueous solution or dispersion of said essential oils in a water carrier. No hydrogen peroxide is disclosed.

SUMMARY OF THE INVENTION

The present invention encompasses a disinfecting composition comprising from 0.1% to 15% by weight of the total composition of hydrogen peroxide and an antimicrobial essential oil, or mixtures thereof.

The present invention further encompasses a process for disinfecting a surface wherein a disinfecting composition according to the present invention, is applied onto said surface.

DETAILED DESCRIPTION OF THE INVENTION

The disinfecting compositions:

The disinfecting compositions according to the present invention comprise from 0.1% to 15% by weight of the total composition of hydrogen peroxide, and an antimicrobial essential oil.

The compositions according to the present invention may be formulated either as liquids or non-liquids (e.g., gel, pasty form or solid form like powder or granular form). In the case where the compositions are formulated as solids, they will be mixed with an appropriate solvent, typically water, before use. The liquid compositions herein may be aqueous compositions or even non-aqueous compositions. Liquid compositions are preferred herein for convenience of use.

As an essential element the compositions according to the present invention comprise hydrogen peroxide.

It is believed that the presence of hydrogen peroxide, in the compositions of the present invention contribute to the disinfection properties of said compositions. Indeed, hydrogen peroxide may attack the vital function of the microorganism cells, for example, it may inhibit the assembling of ribosomes units within the cytoplasm of the microorganism cells. Also hydrogen peroxide is a strong oxidizer that generates hydroxyl free radicals which attack proteins and nucleic acids. Furthermore, the presence of hydrogen peroxide provides strong stain removal benefits which are particularly noticeable for example in laundry and hard surfaces applications.

The compositions herein comprise from 0.1% to 15% by weight of the total composition of hydrogen peroxide, preferably from 0.5% to 10%, and more preferably from 1% to 8%.

As a second essential ingredient, the compositions according to the present invention comprise an antimicrobial essential oil, or mixtures thereof. Typically, the compositions herein comprise at least 0.003% by weight of the total composition of said antimicrobial essential oil, or mixtures thereof, preferably from 0.006% to 10%, more preferably from 0.2% to 4% and most preferably from 0.2% to 2%.

Suitable antimicrobial essential oils to be used in the compositions herein are those essential oils which exhibit antimicrobial activity. It is speculated that said antimicrobial essential oils act as proteins denaturing agents. Said antimicrobial oils contribute to the safety profile of the compositions of the present invention when used to disinfect any surface. A further advantage of said antimicrobial essential oils is that they impart pleasant odor to the disinfecting compositions of the present invention without the need of adding a perfume. Indeed, the disinfecting compositions according to the present invention deliver not only excellent disinfecting properties on clean surfaces to be disinfected but also good scent while being safe to the surfaces.

Suitable antimicrobial essential oils to be used herein include, but are not limited to, the oils obtained from thyme, lemongrass, citrus, lemons, oranges, anise, clove, aniseed, cinnamon, geranium, roses, mint, peppermint, lavender, citronella, eucalyptus, peppermint, camphor, sandalwood, cedar, rosmarin, pine, vervain fleagrass, lemongrass, ratanhiae and mixtures thereof. Particularly preferred to be used herein are eucalyptus oil, thyme oil, clove oil, cinnamon oil, geranium oil, eucalyptus oil, peppermint oil, mint oil and mixtures thereof.

It has now been found that the compositions of the present invention comprising from 0.1% to 15% by weight of hydrogen peroxide and said antimicrobial essential oil or mixtures thereof deliver improved safety on surfaces, e.g., on hard-surfaces and on fabrics like silk, wool and the like, while delivering excellent disinfection performance on clean surfaces even when used under highly diluted conditions as compared to the same composition with a peracid instead of said hydrogen peroxide.

An advantage associated to the present invention is that when using said compositions to disinfect colored fabrics, the color damage is also reduced while delivering excellent disinfection performance on said fabrics, even when used under highly diluted conditions. Indeed, the color change and/or decoloration observed when treating colored fabrics with a composition according to the present invention comprising hydrogen peroxide and said antimicrobial essential oil or mixtures thereof, is reduced, while delivering excellent disinfection performance on said fabrics even when used under highly diluted conditions, as compared to the color change and/or decoloration observed when using the same composition but with a peracid instead of said hydrogen peroxide.

Surface safety may be evaluated on surfaces like fabrics by measuring the tensile strength of said fabrics. The tensile strength of a fabric may be measured by employing the Tensile Strength method. This method consists of measuring the tensile strength of a given fabric by stretching said fabric until it breaks. The force, expressed in Kg, necessary to break the fabric is the "Ultimate Tensile Stress" and may be measured with "The Stress-Strain INSTRON Machine".

Excellent disinfection is obtained with the compositions of the present inventions on a variety of microorganisms including Gram positive bacteria like Staphylococcus aureus, and Gram negative bacteria like Pseudomonas aeroginosa as well as on fungi like Candida albicans present on clean surfaces, i.e., any surface being substantially free of organic and/or inorganic soils, even if used in highly diluted conditions.

Disinfection properties of a composition may be measured by the bactericidal activity of said composition. A test method suitable to evaluate the bactericidal activity of a composition on clean surfaces is described in European Standard, prEN 1040, CEN/TC 216 N 78, dated November 1995 issued by the European committee for standardisation, Brussels. European Standard, prEN 1040, CEN/TC 216 N 78, specifies a test method and requirements for the minimum bactericidal activity of a disinfecting composition. The test is passed if the bacterical colonies forming units (cfu) are reduced from a $10^7$ cfu (initial level) to a $10^2$ cfu (final level after contact with the disinfecting product), i.e. a $10^5$ reduction of the viability is necessary. The compositions according to the present invention pass this test under clean conditions, even if used in highly diluted conditions.

Another test method suitable to evaluate the bactericidal activity of the present compositions on clean surfaces is AFNOR T72-190® and T72-301®

In the preferred embodiment, the compositions according to the present invention are aqueous liquid cleaning compositions. Said aqueous compositions have preferably a pH as is of not more than 12.0, more preferably from 2 to 6, and most preferably from 3 to 5. The pH of the compositions can be adjusted by using organic acids like citric acid, succinic acid, acetic acid, aspartic acid, lactic acid and the like, or inorganic acids, or alkalinising agents.

The compositions of the present invention may further comprise surfactants known to those skilled in the art including nonionic, anionic, cationic, amphoteric and/or zwitterionic surfactants. Said surfactants are desirable as they contribute to the cleaning performance of the compositions herein.

Typically, the compositions according to the present invention comprise up to 50% by weight of the total composition of a surfactant, or mixtures thereof, preferably from 0.01% to 30% and more preferably from 0.1% to 25%.

Accordingly, the compositions of the present invention may preferably comprise an amphoteric surfactant, or mixtures thereof. Suitable amphoteric surfactants to be used herein include betaine and sulphobetaine surfactants, derivatives thereof or mixtures thereof. Said betaine or sulphobetaine surfactants are preferred herein as they contribute to the disinfecting properties of the compositions herein. Indeed, they help disinfection by increasing the permeability of the bacterial cell wall, thus allowing other active ingredients to enter the cell.

Furthermore, due to the mild action profile of said betaine or sulphobetaine surfactants, the compositions herein comprising them may be particularly suitable for the cleaning of delicate surfaces, e.g. delicate laundry or hard-surfaces in contact with food and/or babies. Betaine and sulphobetaine surfactants are also extremely mild to the skin and/or other surfaces to be treated.

Suitable betaine and sulphobetaine surfactants to be used in the compositions of the present invention are the betaine/sulphobetaine and betaine-like detergents wherein the molecule contains both basic and acidic groups which form an inner salt giving the molecule both cationic and anionic hydrophilic groups over a broad range of pH values. Some common examples of these detergents are described in U.S. Pat. Nos. 2,082,275, 2,702,279 and 2,255,082, incorporated herein by reference. Preferred betaine and sulphobetaine surfactants herein are according to the formula

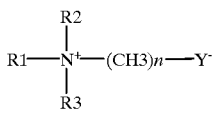

wherein R1 is an alkyl radical containing from 1 to 24 carbon atoms, preferably from 8 to 18, and more preferably from 12 to 14, wherein R2 and R3 contain from 1 to 3 carbon atoms, and preferably 1 carbon atom, wherein n is an integer from 1 to 10, preferably from 1 to 6, and more preferably is 1, Y is selected from the group consisting of carboxyl and sulfonyl radicals and wherein the sum of R1, R2 and R3 radicals is from 14 to 24 carbon atoms, or mixtures thereof.

Examples of particularly suitable betaine surfactants include C2–C18 alkyl dimethyl betaine such as coconutbetaine and C10–C16 alkyl dimethyl betaine such as laurylbetaine.

Coconutbetaine is commercially available from Seppic under the trade name of Amonyl 265®. Laurylbetaine is commercially available from Albright & Wilson under the trade name Empigen BB/L®.

Other suitable amphoteric surfactants to be used herein include amine oxides or mixtures thereof. Amine oxides are preferred herein as they contribute to the disinfecting properties of the compositions herein. Indeed, they help disinfection by disrupting the cell wall/membrane of the bacteria, thus allowing other antimicrobial ingredients to enter the cell and for example attack the inner part of the cell.

Suitable amine oxides to be used herein have the following formula $R_1R_2R_3NO$ wherein each of R1, R2 and R3 is independently a saturated linear or branched hydrocarbon chain containing from 1 to 30 carbon atoms. Suitable amine oxides to be used according to the present invention are amine oxides having the following formula $R_1R_2R_3NO$ wherein R1 is a hydrocarbon chain containing from 1 to 30 carbon atoms, preferably from 6 to 20, more preferably from 6 to 14 and most preferably from 8 to 10, and wherein R2 and R3 are independently substituted or unsubstituted, linear or branched hydrocarbon chains containing from 1 to 4 carbon atoms, preferably of from 1 to 3 carbon atoms, and more preferably are methyl groups. R1 may be a saturated linear or branched hydrocarbon chain.

Preferred amine oxides for use herein are for instance natural blend C8–C10 amine oxides as well as C12–C16 amine oxides commercially available from Hoechst.

In a preferred embodiment of the present invention where the compositions herein are particularly suitable for the disinfection of a hard-surface, the surfactant is typically a surfactant system comprising an amine oxide and a betaine or sulphobetaine surfactant, preferably in a weight ratio of amine oxide to betaine or sulphobetaine of 2:1 to 100:1, more preferably of 6:1 to 100:1 and most preferably 10:1 to 50:1. The use of such a surfactant system in the compositions herein suitable for disinfecting a hard-surface, provides effective cleaning performance and provides shine on the cleaned surfaces, i.e., the amount of filming/streaking left on the cleaned surface that has been treated with said compositions is minimal.

The compositions herein may also preferably comprise an anionic surfactant or mixtures thereof. Particularly suitable anionic surfactants to be used herein include water-soluble salts or acids of the formula $ROSO_3M$ wherein R is preferably a $C_6$–$C_{24}$ hydrocarbyl, preferably an alkyl or hydroxyalkyl having a $C_8$–$C_{20}$ alkyl component, more preferably a $C_8$–$C_{16}$ alkyl or hydroxyalkyl, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethylammonium and dimethyl piperdinium cations and quaternary ammonium cations derived from alkylamines such as ethylamine, diethylamine, triethylamine, and mixtures thereof, and the like).

Other suitable anionic surfactants to be used herein include alkyl-diphenyl-ether-sulphonates and alkyl-carboxylates. Other anionic surfactants can include salts (including, for example, sodium, potassium, ammonium, and substituted ammonium salts such as mono-, di- and triethanolamine salts) of soap, $C_9$–$C_{20}$ linear alkylbenzenesulfonates, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl ester sulfonates such as $C_{14-16}$ methyl ester sulfonates; acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinate (especially saturated and unsaturated $C_{12}$–$C_{18}$ monoesters) diesters of sulfosuccinate (especially saturated and unsaturated $C_6$–$C_{14}$ diesters), acyl sarcosinates, sulfates of alkylpolysaccharides such as the sulfates of alkylpolyglucoside (the nonionic nonsulfated compounds being described below), branched primary alkyl sulfates, alkyl polyethoxy carboxylates such as those of the formula $RO(CH_2CH_2O)_kCH_2COO-M^+$ wherein R is a $C_8$–$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23.

Preferred anionic surfactants for use in the compositions herein are the C8–C16 alkyl sulfonates, C8–C16 alkyl sulfates, C8–C16 alkyl alkoxylated sulfates (e.g., C8–C16 alkyl ethoxylated sulfates), and mixtures thereof. Such anionic surfactants are preferred herein as it has been found that they contribute to the disinfecting properties of a disinfecting compositions comprising hydrogen peroxide and/or an antimicrobial essential oil. For example, C8–C16 alkyl sulfate acts by disorganizing the bacteria cell menbrane, inhibiting enzymatic activities, interrupting the cellular transport and/or denaturing cellular proteins. Indeed, it is speculated that the improved disinfecting performance associated with the addition of an anionic surfactant, especially a C8–C16 alkyl sulfonate, a C8–C16 alkyl sulfate and/or a C8–C16 alkyl alkoxylated sulfate, in for example a composition of the present invention, is likely due to multiple mode of attack of said surfactant against the bacteria. Thus, another aspect of the present invention is the use of an anionic surfactant, especially a C8–C16 alkyl sulfonate, a C8–C16 alkyl sulfate and/or a C8–C16 alkyl alkoxylated sulfate, in a disinfecting composition comprising a hydrogen peroxide and/or an antimicrobial essential oil, to improve the disinfecting properties of said composition on gram negative and/or gram positive bacteria.

Suitable nonionic surfactants for use herein are fatty alcohol ethoxylates and/or propoxylates which are commercially available with a variety of fatty alcohol chain lengths and a variety of ethoxylation degrees. Indeed, the HLB values of such alkoxylated nonionic surfactants depend essentially on the chain length of the fatty alcohol, the nature of the alkoxylation and the degree of alkoxylation. Surfactant catalogues are available which list a number of surfactants, including nonionics, together with their respective HLB values.

Particularly suitable for use herein as nonionic surfactants are hydrophobic nonionic surfactants having an HLB (hydrophilic-lipophilic balance) below 16, preferably below 15 and more preferably below 14. Those hydrophobic nonionic surfactants have been found to provide good grease cutting properties.

Preferred hydrophobic nonionic surfactants to be used in the compositions according to the present invention are surfactants having an HLB below 16 and being according to the formula $RO-(C_2H_4O)_n(C_3H_6O)_mH$, wherein R is a $C_6$ to $C_{22}$ alkyl chain or a $C_6$ to $C_{28}$ alkyl benzene chain, and wherein n+m is from 0 to 20 and n is from 0 to 15 and m is from 0 to 20, preferably n+m is from 1 to 15 and, n and m are from 0.5 to 15, more preferably n+m is from 1 to 10 and, n and m are from 0 to 10. The preferred R chains for use herein are the $C_8$ to $C_{22}$ alkyl chains. Accordingly, suitable hydrophobic nonionic surfactants for use herein are Dobanol $^R$ 91-2.5 (HLB=8.1; R is a mixture of C9 and $C_{11}$ alkyl chains, n is 2.5 and m is 0), or Lutensol $^R$ TO3 (HLB=8; R is a $C_{13}$ alkyl chains, n is 3 and m is 0), or Lutensol $^R$ AO3 (HLB=8; R is a mixture of $C_{13}$ and $C_{15}$ alkyl chains, n is 3 and m is 0), or Tergitol $^R$ 25L3 (HLB=7.7; R is in the range of $C_{12}$ to $C_{15}$ alkyl chain length, n is 3 and m is 0), or Dobanol $^R$ 23-3 (HLB=8.1; R is a mixture of $C_{12}$ and $C_{13}$ alkyl chains, n is 3 and m is 0), or Dobanol $^R$ 23-2 (HLB=6.2; R is a mixture of $C_{12}$ and $C_{13}$ alkyl chains, n is 2 and m is 0), or Dobanol $^R$ 45-7 (HLB=11.6; R is a mixture of $C_{14}$ and $C_{15}$ alkyl chains, n is 7 and m is 0) Dobanol $^R$ 23-6.5 (HLB=11.9; R is a mixture of $C_{12}$ and $C_{13}$ alkyl chains, n is 6.5 and m is 0), or Dobanol $^R$ 25-7 (HLB=12; R is a mixture of $C_{12}$ and $C_{15}$ alkyl chains, n is 7 and m is 0), or Dobanol $^R$ 91-5 (HLB=11.6; R is a mixture of $C_9$ and $C_{11}$ alkyl chains, n is 5 and m is 0), or Dobanol $^R$ 91-6 (HLB=12.5; R is a mixture of $C_9$ and $C_{11}$ alkyl chains, n is 6 and m is 0), or Dobanol $^R$ 91-8 (HLB=13.7; R is a mixture of $C_9$ and $C_{11}$ alkyl chains, n is 8 and m is 0), Dobanol $^R$ 91-10 (HLB=14.2; R is a mixture of $C_9$ to $C_{11}$ alkyl chains, n is 10 and m is 0), or mixtures thereof. Preferred herein are Dobanol $^R$ 91-2.5 , or Lutensol $^R$ TO3, or Lutensol $^R$ AO3, or Tergitol $^R$ 25L3, or Dobanol $^R$ 23-3, or Dobanol $^R$ 23-2, or mixtures thereof. These Dobanol$^R$ surfactants are commercially available from SHELL. These Lutensol$^R$ surfactants are commercially available from BASF and these Tergitol $^R$ surfactants are commercially available from UNION CARBIDE.

Other suitable surfactants also include C6–C20 conventional soaps (alkali metal salt of a C6–C20 fatty acid, preferably sodium salts).

The compositions according to the present invention may comprise as preferred optional ingredients further antimicrobial ingredients that contribute to the antimicrobial activity of compositions of the present invention. Such antimicrobial ingredients include parabens like ethyl paraben, propyl paraben, methyl paraben, glutaraldehyde or mixtures thereof.

The compositions herein may further comprise a chelating agent as a preferred optional ingredient. Suitable chelating agents may be any of those known to those skilled in the art such as the ones selected from the group comprising phosphonate chelating agents, aminophosphonate chelating agents, substituted heteroaromatic chelating agents, amino carboxylate chelating agents, other carboxylate chelating agents, polyfunctionally-substituted aromatic chelating agents, biodegradable chelating agents like ethylene diamine N,N'- disuccinic acid, or mixtures thereof.

Suitable phosphonate chelating agents to be used herein include etidronic acid (1-hydroxyethylene-diphosphonic acid (HEDP)), and/or alkali metal ethane 1-hydroxydiphosphonates.

Suitable amino phosphonate chelating agents to be used herein include amino alkylene poly (alkylene phosphonates), nitrilotris(methylene)triphosphonates, ethylene diamine tetra methylene phosphonates, and/or diethylene triamine penta methylene phosphonates. Preferred aminophosphonate chelating agents to be used herein are diethylene triamine penta methylene phosphonates.

These phosphonate/amino phosphonate chelating agents may be present either in their acid form or as salts of different cations on some or all of their acid functionalities. Such phosphonate/amino phosphonate chelating agents are commercially available from Monsanto under the trade name DEQUEST®.

Substituted heteroaromatic chelating agents to be used herein include hydroxypiridine-N-oxide or a derivative thereof.

Suitable hydroxy pyridine N-oxides and derivatives thereof to be used according to the present invention are according to the following formula:

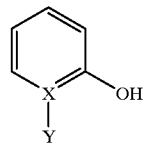

wherein X is nitrogen, Y is one of the following groups oxygen, —CHO, —OH, —(CH2)n—COOH, wherein n is an integer of from 0 to 20, preferably of from 0 to 10 and more preferably is 0, and wherein Y is preferably oxygen. Accordingly particularly preferred hydroxy pyridine N-oxides and derivatives thereof to be used herein is 2-hydroxy pyridine N-oxide.

Hydroxy pyridine N-oxides and derivatives thereof may be commercially available from Sigma.

Polyfunctionally-substituted aromatic chelating agents may also be useful in the compositions herein. See U.S. Pat. No. 3,812,044, issued May 21, 1974, to Connor et al. Preferred compounds of this type in acid form are dihydroxydisulfobenzenes such as 1,2-dihydroxy -3,5-disulfobenzene.

A preferred biodegradable chelating agent for use herein is ethylene diamine N,N'- disuccinic acid, or alkali metal, or alkaline earth, ammonium or substitutes ammonium salts thereof or mixtures thereof. Ethylenediamine N,N'- disuccinic acids, especially the (S,S) isomer have been extensively described in U.S. Pat. No. 4,704,233, Nov. 3, 1987 to Hartman and Perkins. Ethylenediamine N,N'- disuccinic acid is, for instance, commercially available under the tradename ssEDDS® from Palmer Research Laboratories. Ethylene diamine N,N'- disuccinic acid is particularly suitable to be used in the compositions of the present invention.

Suitable amino carboxylate chelating agents useful herein include ethylene diamine tetra acetates, diethylene triamine pentaacetates, diethylene triamine pentoacetate (DTPA), N-hydroxyethylethylenediamine triacetates, nitrilotriacetates, ethylenediamine tetraproprionates, triethylenetetraaminehexa-acetates, ethanoldiglycines, propylene diamine tetracetic acid (PDTA) and methyl glycine di-acetic acid (MGDA), both in their acid form, or in their alkali metal, ammonium, and substituted ammonium salt forms. Particularly suitable to be used herein are diethylene triamine penta acetic acid (DTPA), propylene diamine tetracetic acid (PDTA) which is, for instance, commercially available from BASF under the trade name Trilon FS® and methyl glycine di-acetic acid (MGDA).

Further carboxylate chelating agents to be used herein includes malonic acid, salicylic acid, glycine, aspartic acid, glutamic acid, or mixtures thereof.

Said chelating agents, especially phosphonate chelating agents like diethylene triamine penta methylene phosphonates, are particularly preferred in the compositions according to the present invention as they have been found to further contribute to the disinfecting properties of hydrogen peroxide. Thus, another aspect of the present invention is the use of a chelating agent, especially a phosphonate chelating agent like diethylene triamine penta methylene phosphonate, in a disinfecting composition comprising hydrogen peroxide, to improve the disinfecting properties of said composition on gram negative and/or gram positive bacteria.

Typically, the compositions according to the present invention comprise up to 5% by weight of the total composition of a chelating agent, or mixtures thereof, preferably from 0.002% to 3% by weight and more preferably from 0.002% to 1.5%.

The compositions herein may comprise a radical scavenger as a preferred optional ingredient. Suitable radical scavengers for use herein include the well-known substituted mono and di hydroxy benzenes and derivatives thereof, alkyl- and aryl carboxylates and mixtures thereof. Preferred radical scavengers for use herein include di-tert-butyl hydroxy toluene (BHT), p-hydroxy-toluene, hydroquinone (HQ), di-tert-butyl hydroquinone (DTBHQ), mono-tert-butyl hydroquinone (MTBHQ), tert-butyl-hydroxy anysole (BHA), p-hydroxy-anysol, benzoic acid, 2,5-dihydroxy benzoic acid, 2,5-dihydroxyterephtalic acid, toluic acid, catechol, t-butyl catechol, 4-allyl-catechol, 4-acetyl catechol, 2-methoxy-phenol, 2-ethoxy-phenol, 2-methoxy-4-(2-propenyl)phenol, 3,4-dihydroxy benzaldehyde, 2,3-dihydroxy benzaldehyde, benzylamine, 1,1,3-tris(2-methyl-4-hydroxy-5-t-butylphenyl) butane, tert-butyl-hydroxy-anyline, p-hydroxy anyline as well as n-propyl-gallate. Highly preferred for use herein are di-tert-butyl hydroxy toluene, which is for example commercially available from SHELL under the trade name IONOL CP® and/or tert-butyl-hydroxy anysole. These radical scavengers further contribute to the stability of the hydrogen peroxide-containing compositions herein.

Typically, the compositions according to the present invention comprise up to 5% by weight of the total composition of a radical scavenger, or mixtures thereof, preferably from 0.001% to 1.5% by weight and more preferably from 0.01% to 1%.

The compositions herein may comprise as a preferred optional ingredient a solvent or mixtures thereof. When used, solvents will, advantageously, give an enhanced cleaning to the compositions herein. Suitable solvents for incorporation in the compositions according to the present invention include propylene glycol derivatives such as n-butoxypropanol or n-butoxypropoxypropanol, water-soluble CARBITOL® solvents or water-soluble CELLOSOLVE® solvents. Water-soluble CARBITOL® solvents are compounds of the 2-(2-alkoxyethoxy)ethanol class wherein the alkoxy group is derived from ethyl, propyl or butyl. A preferred water-soluble carbitol is 2-(2-butoxyethoxy)ethanol also known as butyl carbitol. Water-soluble CELLOSOLVE® solvents are compounds of the 2-alkoxyethoxyethanol class, with 2-butoxyethoxyethanol being preferred. Other suitable solvents are benzyl alcohol, methanol, ethanol, isopropyl alcohol and diols such as 2-ethyl-1,3-hexanediol and 2,2,4-trimethyl-1,3-pentanediol and mixture thereof. Preferred solvents for use herein are n-butoxypropoxypropanol, butyl carbitol® and mixtures thereof. Most preferred solvents for use herein are butyl carbitol®, benzyl alcohol and isopropanol.

The solvents may typically be present within the compositions of the invention at a level up to 15% by weight, preferably from 2% to 7% by weight of the composition.

The compositions herein may further comprise a variety of other optional ingredients such as buffers (e.g. borate buffers), builders, stabilisers, bleach activators, soil suspenders, dye transfer agents, brighteners, perfumes, anti dusting agents, enzymes, dispersant, dye transfer inhibitors, pigments, perfumes and dyes.

Packaging form of the compositions:

The compositions herein may be packaged in a variety of suitable detergent packaging known to those skilled in the art. The liquid compositions herein may desirably be packaged in manually operated spray dispensing containers, which are usually made of synthetic organic polymeric plastic materials. Accordingly, the present invention also encompasses liquid disinfecting compositions comprising hydrogen peroxide and an antimicrobial essential oil packaged in a spray dispenser, preferably in a trigger spray dispenser or pump spray dispenser.

Indeed, said spray-type dispensers allow to uniformly apply to a relatively large area of a surface to be disinfected the liquid disinfecting compositions suitable to be used according to the present invention, thereby contributing to disinfection properties of said compositions. Such spray-type dispensers are particularly suitable to disinfect vertical surfaces.

Suitable spray-type dispensers to be used according to the present invention include manually operated foam trigger-type dispensers sold for example by Specialty Packaging Products, Inc. or Continental Sprayers, Inc. These types of dispensers are disclosed, for instance, in U.S. Pat. No. 4,701,311 to Dunning et al. and U.S. Pat. No. 4,646,973 and U.S. Pat. No. 4,538,745 both to Focarracci. Particularly preferred to be used herein are spray-type dispensers such as T 8500® or T 8900®commercially available from Continental Spray International, or T 8100® commercially available from Canyon, Northern Ireland. In such a dispenser the liquid composition is divided in fine liquid droplets resulting in a spray that is directed onto the surface to be treated. Indeed, in such a spray-type dispenser the composition contained in the body of said dispenser is directed through the spray-type dispenser head via energy communicated to a pumping mechanism by the user as said user activates said pumping mechanism. More particularly, in said spray-type dispenser head the composition is forced against an obstacle, e.g. a grid or a cone or the like, thereby providing shocks to help atomise the liquid composition, i.e. to help the formation of liquid droplets.

The compositions of the present invention may also be executed in the form of wipes. By "wipes" it is meant herein disposable towels impregnated with a liquid composition according to the present invention. Accordingly, the present invention also encompasses wipes, e.g. disposable paper towels, impregnated with a liquid composition according to the present invention. In the preferred execution said wipes are wetted with said liquid compositions. Preferably said wipes are packaged in a plastic box. The advantage of this execution is a faster usage of a disinfecting composition by the user, this even outside the house, i.e. there is no need to pour the liquid compositions according to the present invention on the surfaces to be treated/disinfect and to dry it out with a cloth. In other words, wipes allow disinfection of surfaces in one step.

The Process of disinfecting:

The present invention encompasses a process for disinfecting surfaces wherein a composition according to the present invention is applied onto said surfaces.

By "surface" it is meant herein any surface including animate surface like human skin, mouth, teeth, and inanimate surfaces. Inanimate surfaces include, but are not limited to, hard-surfaces typically found in houses like kitchens, bathrooms, or in car interiors, e.g., tiles, walls, floors, chrome, glass, smooth vinyl, any plastic, plastified wood, table top, sinks, cooker tops, dishes, sanitary fittings such as sinks, showers, shower curtains, wash basins, WCs and the like, as well as fabrics including clothes, curtains, drapes, bed linens, bath linens, table cloths, sleeping bags, tents, upholstered furniture and the like, and carpets. Inanimate surfaces also include household appliances including, but not limited to, refrigerators, freezers, washing machines, automatic dryers, ovens, microwave ovens, dishwashers and so on.

In the process of disinfecting surfaces according to the present invention said compositions may be applied to the surface to be disinfected in its neat form or in its diluted form.

By "diluted form" it is meant herein that the compositions to be used in the disinfection process herein being either in a liquid or solid form may be diluted by the user typically up to 100 times their weight of water, preferably into 80 to 30 times their weight of water, and more preferably 60 to 40 times.

In the preferred embodiment of the process of the present invention wherein said composition is applied to a hard-surface to be disinfected in its diluted form, it is not necessary to rinse the surface after the composition has been applied, indeed no visible residues are left onto the surface.

The present invention will be further illustrated by the following examples.

EXAMPLES

The following compositions were made by mixing the listed ingredients in the listed proportions (weight % unless otherwise specified). These compositions passed the prEN 1040 test of the European committee of standardisation. These compositions provide excellent disinfection when used neat or diluted, e.g. at 1:100, 1:25, 1:50 dilution levels, on clean surfaces while delivering also excellent surface safety and skin mildness.

| | Compositions | | | | | |
|---|---|---|---|---|---|---|
| | I | II | III | IV | V | VI |
| Hydrogen peroxide | 7.0 | 6.0 | 6.0 | 6.0 | 2.0 | 7.0 |
| Thyme oil | 0.5 | — | — | 0.5 | — | 0.5 |
| Clove oil | — | 1.0 | — | — | 0.1 | 0.5 |
| Geranium oil | 0.5 | — | — | — | — | — |
| Eucalyptus oil | — | — | 1.0 | — | — | 0.5 |
| Water and minors | | | up to 100% | | | |
| H2SO4 up to pH4 | | | | | | |

| | VII | VIII | IX | X |
|---|---|---|---|---|
| Hydrogen peroxide | 7.0 | 6.0 | 1.0 | 2.0 |
| Thyme oil | — | 0.5 | — | — |
| Clove oil/eucalyptus oil (1:1) | 1.0 | — | 0.5 | 0.05 |
| Geranium oil | — | 0.5 | — | — |
| Water and minors | | up to 100% | | |
| H2SO4 up to pH 4 | | | | |

| | XI | XII | XIII | XIV | XV |
|---|---|---|---|---|---|
| Hydrogen peroxide | 7.0 | 6.0 | 1.0 | 2.0 | 1.0 |
| C10 alkyl sulfate | 3.0 | 4.0 | — | 1.5 | — |
| C10 Amine Oxide | 1.5 | — | 1.5 | — | 0.9 |
| Lauryl betaine | — | — | — | — | 0.05 |
| Thyme oil | — | 0.5 | — | — | 0.03 |
| Eucalyptus oil | — | — | — | — | 0.02 |
| Clove oil/eucalyptus oil (1:1) | 1.0 | — | 0.5 | 0.05 | — |
| Geranium oil | — | 0.5 | — | — | — |
| Water and minors | | | up to 100% | | |
| H2SO4 up to pH4 | | | | | |

What is claimed is:

1. A disinfecting composition comprising
   i) hydrogen peroxide in an amount of 0.1% to 15% by weight of the total composition;
   ii) an antimicrobial essential oil; and
   iii) a surfactant;
   wherein said surfactant is amphoteric corresponding to formula:

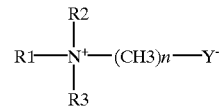

(a.)

wherein R1 is an alkyl radical containing from 1 to 24 carbon atoms, wherein R2 and R3 contain from 1 to 3 carbon atoms wherein n is an integer from 1 to 10, Y is selected from the group consisting of carboxyl and sulfonyl radicals and
   wherein the sum of R1, R2 and R3 radicals is from about 14 to about 24 carbon atoms; or b. $R_1R_2R_3NO$ wherein each of R1, R2 and R3 is independently a saturated linear or branched hydrocarbon chain containing from 1 to 30 carbon atoms, and wherein R2 R3 are independently substituted or unsubstituted, linear or branched hydrocarbon chains containing from 1 to 4 carbon atoms.

2. A composition according to claim 1 wherein said composition further comprises another antimicrobial ingredient selected from the group consisting of glutaraldehyde, ethyl paraben, propyl paraben, methyl paraben and mixtures thereof.

3. A composition according to claim 1 wherein said composition further comprises a chelating agent selected from the group consisting of phosphonate chelating agents, aminophosphonate chelating agents, substituted heteroaromatic chelating agents, amino carboxylate chelating agents, polyfunctionally-substituted aromatic chelating agents, ethylene diamine N,N'- disuccinic acid, and mixtures thereof.

4. A composition according to claim 1 wherein said composition further comprises at least an optional ingredient selected from the group consisting of radical scavengers, solvents, buffers, builders, stabilizers, bleach activators, soil suspenders, dye transfer agents, perfumes, anti dusting agents, enzymes, dispersant, dye transfer inhibitors, pigments, dyes and mixtures thereof.

5. A composition according to claim 1 wherein said composition is a liquid composition having a pH of no more than 12.

6. A wipe impregnated with a disinfecting composition according to claim 5.

7. A disinfecting composition according to claim 5, packaged in a spray dispenser.

8. A method for disinfection of gram negative and/or gram positive bacteria in the mouth by contacting the oral surface using the composition according to claim 3.

9. A composition according to claim 1 wherein said hydrogen peroxide is from 0.5% to 10% by weight of the total composition.

10. A composition according to claim 9 wherein said antimicrobial essential oil is selected from the group consisting of thyme oil, lemongrass oil, citrus oil, lemon oil, orange oil, anise oil, clove oil, aniseed oil, cinnamon oil, geranium oil, rose oil, lavender oil, citronella oil, eucalyptus oil, peppermint oil, mint oil, camphor oil, sandalwood oil, cedar oil, rosmarin oil, pine oil, vervain oil, fleagrass oil, ratanhiae oil and mixtures thereof.

11. A composition according to claim 1 wherein said composition comprises said antimicrobial essential oil in an amount of at least 0.003% by weight of the total composition.

12. A composition according to claim 11 for disinfecting the mouth wherein said antimicrobial essential oil is selected from the group consisting of thyme oil, clove oil, geranium oil, rose oil, eucalyptus oil, and mixtures thereof.

13. A composition according to claim 12 wherein said composition comprises said antimicrobial essestial oil in an amount of from about 0.005% to 2.0% by weight of the total composition.

14. A composition according to claim 13 wherein said antimicrobial essential oil is selected from the group consisting of clove oil, geranium oil, eucalyptus oil, and mixtures thereof.

15. A composition according to claim 14 wherein the antimicrobial essential oils are individually from about 0.05% to about 1% by weight of the total composition.

16. A process of disinfecting a surface wherein a composition according to claim 13, is applied onto said surface.

17. A process according to claim 16 wherein said composition is applied onto said surface after having been diluted up to 100 times its weight of water.

* * * * *